Nov. 7, 1933. C WEIGAND Plant Pat. 79
ROSE
Filed Feb. 11, 1933
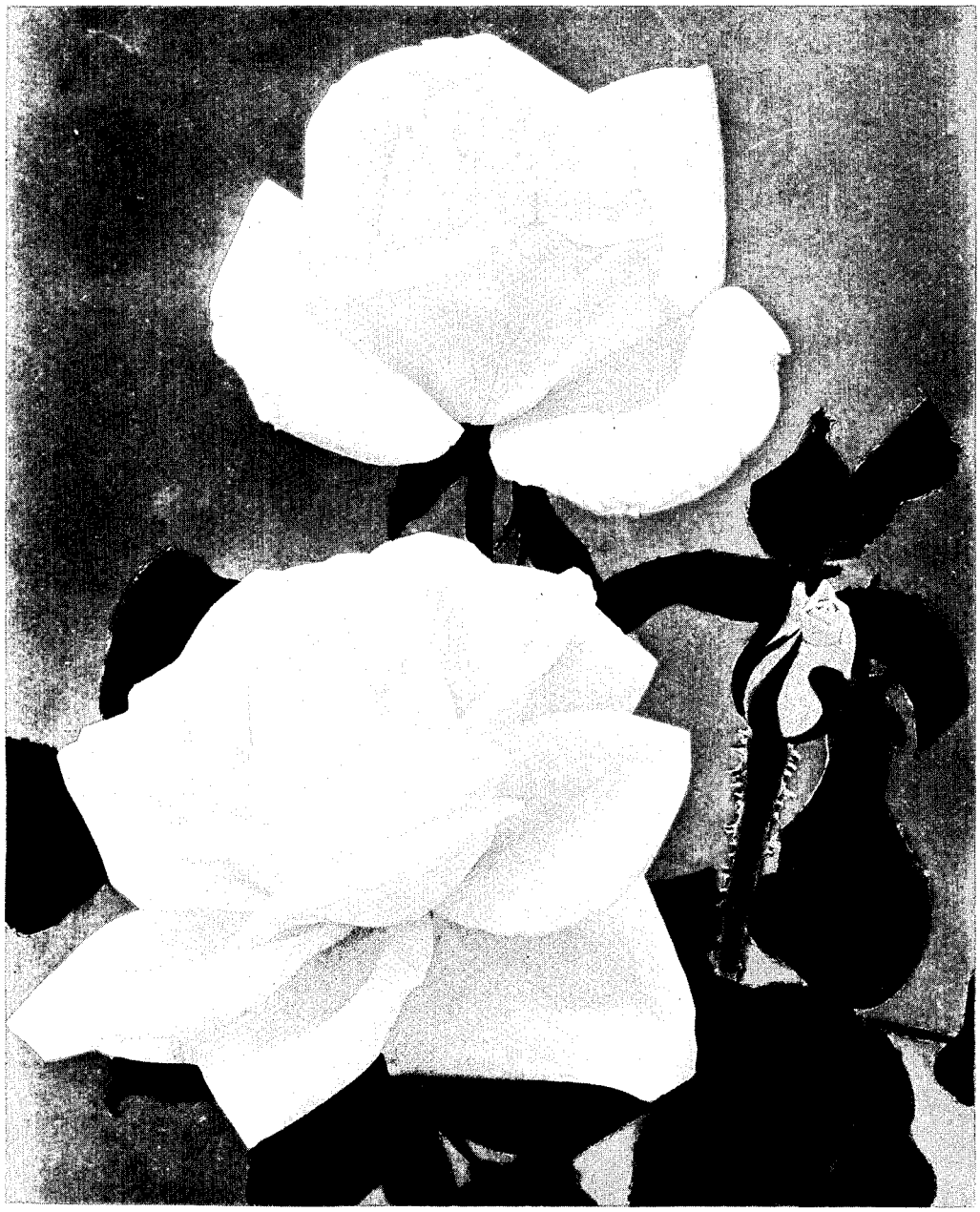
INVENTOR
Christoph Weigand
By Orville M. Kile
Plant Patent Agent Patented Nov. 7, 1933

Plant Pat. 79

UNITED STATES PATENT OFFICE

79

ROSE

Christoph Weigand, Soden, Germany, assignor to
Paul J. Howard, Los Angeles, Calif.

Application February 11, 1933. Serial No. 656,349

1 Claim. (Cl. 47—61)

My new variety of rose is classed as a hybrid perpetual of the larger size. I developed this new rose by crossing the Frau Karl Druschki and the Souvenir de Claudius Pernet. The object of my invention is to provide a vigorous growing rose resembling the Frau Karl Druschki in form, size and shape, but having a distinctive pink color and fragrant odor and possessing the Pernetian qualities of freer blooming and better distribution of blossoms throughout the year.

The accompanying illustration shows in full color a tightly rolled bud and two of the opened flowers of this new variety, as well as some of the foliage and a characteristic stem.

The plant under ordinary greenhouse conditions attains a height of six to seven feet. It is a vigorous grower and unlike most hybrids between Druschki and Pernetiana varieties, it produces no blind wood. Each shoot is surmounted by buds and flowers of very large size and forms no further side shoots. When grown in greenhouse benches spaced 15 by 15 inches, the average number of flowers produced per plant per year is about 36. The growth is upright. The plant is completely hardy and provides a particularly beautiful giant flowering variety suitable for garden as well as for greenhouse use.

*Stems.*—Dark green, heavily beset with light straw-colored spines, having a reddish cast at the point of adherence to the main stem. The characteristic form of peduncle is tapering from quite thick at the point of attachment to the bud or flower, to moderately thick two inches below the flower.

*Foliage.*—Rich dark green, leathery in texture and practically mildew-proof.

*Buds.*—Are of great length. Before opening they are about one inch thick at the base. Just before opening the buds have a length of 2¾ to 3 inches. They open freely in all weathers and show no tendency whatever to "bull-head."

*Sepals.*—Usually four in number, of great length—1½ to 2 inches—broad, irregular and foliaceous.

*Blossoms.*—Of very large size, averaging 5 inches in diameter on greenhouse grown plants and at certain cool periods they reach a diameter of 6 inches. The form of buds and flowers is practically that of the Frau Karl Druschki and may be described as perfect, with petals more or less incurving. The flower has ample petalage, averaging 35 to 40. The petals are full and rounded with comparatively few rudimentary central petals. The fully opened flower shows an abundance of yellow anthers.

The color is "flesh pink" (Ridgeway's Color Standards and Nomenclature, Plate XIII) to "Venetian pink". While this flesh pink color is rather uniformly distributed over each individual petal, the flower appears to have the deeper Venetian pink tone at the center. The color persists in the fully developed flower even under the most adverse weather conditions. The blossoms have excellent keeping qualities. When cut and placed in water, they remain in almost perfect condition for four or five days.

Moderately fragrant.

This new variety of rose while having blossoms of the size and form of the Frau Karl Druschki, also the same color of leafage and wood, is readily distinguished from that variety by:

1. Its Flesh pink color as compared with the snow white Frau Karl Druschki or the subdued crimson of the Druschki Rubra.
2. Its fragrance, a character lacking in the Frau Karl Druschki.
3. Its more profuse blooming and better distribution of blooms throughout the season.
4. Its habit of producing no blind wood.

Having fully described and disclosed my invention, I claim:

The variety of rose herein described and illustrated, characterized particularly by its blossoms of typical Frau Karl Druschki form, size and texture but having a Flesh pink color and fragrant odor; also by its profuse blooming habits continuing throughout the long season.

CHRISTOPH WEIGAND.